United States Patent
Fevola et al.

(10) Patent No.: US 12,016,942 B2
(45) Date of Patent: Jun. 25, 2024

(54) POTASSIUM HYDROGEN SALTS OF ALKYLHYDROXAMATES AND COMPOSITIONS COMPRISING THE SAME

(71) Applicant: Inolex Investment Corporation, Wilmington, DE (US)

(72) Inventors: Michael J Fevola, Wilmington, DE (US); Zongyu Zhang, Wilmington, DE (US); Robert J. Ferrara, Wilmington, DE (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 17/883,982

(22) Filed: Aug. 9, 2022

(65) Prior Publication Data

US 2023/0073029 A1 Mar. 9, 2023

Related U.S. Application Data

(60) Provisional application No. 63/235,495, filed on Aug. 20, 2021.

(51) Int. Cl.
| | | |
|---|---|---|
| *A61K 8/42* | (2006.01) | |
| *A61K 8/02* | (2006.01) | |
| *A61K 8/34* | (2006.01) | |
| *A61K 8/37* | (2006.01) | |
| *A61K 8/92* | (2006.01) | |
| *A61Q 5/02* | (2006.01) | |
| *A61Q 17/00* | (2006.01) | |
| *A61Q 19/00* | (2006.01) | |

(52) U.S. Cl.
CPC .............. *A61K 8/42* (2013.01); *A61K 8/0291* (2013.01); *A61K 8/345* (2013.01); *A61K 8/37* (2013.01); *A61K 8/92* (2013.01); *A61Q 5/02* (2013.01); *A61Q 17/005* (2013.01); *A61Q 19/007* (2013.01); *A61K 2800/522* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 7,007,805 B2 * | 3/2006 | Hughes | B03D 1/01 252/61 |
| 2003/0152503 A1 * | 8/2003 | Deveau | C22B 34/24 423/140 |
| 2004/0059156 A1 | 3/2004 | Hughes | |
| 2004/0211933 A1 | 10/2004 | Hughes | |
| 2020/0170248 A1 | 6/2020 | Winn | |

OTHER PUBLICATIONS

IMAP Group Assessment Report (published on Nov. 27, 2014 with title Hydroxylamine and its salts: Human health tier II assessment.*
Hope et al. (Inorganica Chimica Acta 363 (2010) 935-943, titled, Spectroscopic characterization of n-octanohydroxamic acid and potassium hydrogen n-octanohydroxamate.*
Hope et al., 'Spectroscopic Characterisation of n-octanohydroxamic acid and potassium hydrogen n-octanohydroxamate', Inorganica Chimica Acta, Dec. 28, 2009, vol. 363, pp. 935-943; p. 936.
International Search Report and Written Opinion for International Patent Application No. PCT/US2022/039801, dated Oct. 26, 2022. Issued by Kari Rodriguez of the ISA/US.

* cited by examiner

*Primary Examiner* — Tigabu Kassa
(74) *Attorney, Agent, or Firm* — COZEN O'CONNOR

(57) ABSTRACT

The present invention relates to potassium hydrogen alkylhydroxamate compounds and compositions and formulations comprising same, processes for preparing the inventive potassium hydrogen alkylhydroxamate compounds, as well as applications thereof including the use of the inventive compounds and compositions in formulations of products or components of products.

22 Claims, 3 Drawing Sheets

POTASSIUM HYDROGEN SALTS OF ALKYLHYDROXAMATES AND COMPOSITIONS COMPRISING THE SAME

CROSS REFERENCE TO RELATED APPLICATIONS

This Application claims priority to U.S. Provisional Application No. 63/235,495, filed Aug. 20, 2021, which is incorporated herein by reference.

FIELD OF INVENTION

The present invention relates to potassium hydrogen salts of alkylhydroxamate compounds and compositions, formulations containing the compounds and compositions, methods of making and using the compounds, compositions, and formulations, and applications thereof that include inter alia cosmetic applications.

BACKGROUND OF THE TECHNOLOGY

Organic acids are well known for preservation of foods, cosmetics, personal care products, and pharmaceuticals. Examples include benzoic acid and sorbic acid.[1,2] These compounds must be present in their acid form to effectively preserve formulations against microbial contamination and growth. As the pH of a formulation increases, the fraction of organic acid present in the active acid form decreases as the fraction in the inactive ionized or salt form increases. This phenomenon depends on the $pK_a$ of the organic acid, whereby the lower the $pK_a$, the lower the formulation pH must be in order for the acid to provide effective preservation. Some $pK_a$ values for various acids are: salicylic acid, $pK_a=3.0$; benzoic acid, $pK_a=4.2$; p-anisic acid, $pK_a=4.5$; levulinic acid, $pK_a=4.6$; and sorbic acid, $pK_a=4.8$.

However, in their acid forms these compounds have limited water solubility and are difficult to dissolve in water, making compounding of formulations difficult. Prior solutions involved making a presolubilized blend of the organic acid using a water-miscible carrier solvent, such as a glycol, polyol, aromatic alcohol, etc. An alternative and more economical solution is to add the organic acid in its salt form, e.g. sodium benzoate or potassium sorbate, for easier dissolution, and then decrease the solution pH using an acid to obtain a uniform solution of the organic acid. Nevertheless, such compounds are generally considered inefficient or ineffective for control microbial contamination and inhibiting microbial growth above pH 5.5 due to their low $pK_a$ values.

Especially useful is caprylhydroxamic acid ("CHA"), which is a chelating agent that also helps protect formulations against microbial contamination and growth. A key advantage of CHA and related $C_6$ to $C_{10}$ alkylhydroxamic acids is that the hydroxamic acid functionality has a much higher $pK_a$ value compared to traditional organic acids, and therefore it remains in the acid form at higher values of solution pH. For example, FIG. 1 shows that CHA ($pK_a \approx 9.4$) exist predominantly in the more beneficial acid form across a much wider range of pH values compared to benzoic and sorbic acids. This greater pH flexibility provides formulators more latitude when selecting ingredients and setting formula specifications.

Like traditional organic acids, CHA and related $C_6$ to $C_{10}$ alkylhydroxamic acids exhibit limited water solubility and are difficult to dissolve in water; however, the corresponding alkali metal salts of CHA and related $C_6$ to $C_{10}$ alkylhydroxamic acids demonstrate significantly greater water solubility and are readily dissolved in aqueous media at higher concentrations than the acid forms. Thus, one would expect to be able to utilize the salt form of CHA or related $C_6$ to $C_{10}$ alkylhydroxamic acids to rapidly dissolve the compound in water and then obtain the acid form in solution by lowering the pH of the resulting solution.

U.S. Pat. No. 7,007,805 B2 to Hughes discloses that potassium salts of alkylhydroxamic acids may be isolated as crystalline solids that are "aggregates" of one equivalent of potassium alkylhydroxamate hydrogen bonded with one equivalent of alkylhydroxamic acid, i.e. $KH(AH)_2$.[3] This finding was confirmed by Hope and co-workers in 2010.[4] However, Hughes is directed to alkaline compositions with pH values great than 11, and teaches away from adding acid and/or lowering pH. Hughes is also concerned with flotation of mineral ores and is silent to applications of alkylhydroxamates for control of microbial growth or microbial contamination.

International Patent Pub. No. WO2009/070736 A1 to Inolex and International Patent Pub. No. WO2010/069957 A1 to Unilever disclose alkylhydroxamic acids and salts, but do not differentiate between sodium or potassium salts, nor do they mention the $KH(AH)_2$ form. The latter also discloses only the monovalent salts (i.e., MAH, where M is an alkali metal and AH is an alkylhydroxamate), and compositions buffered to pH 7 to 8 and formulating with bases, e.g. sodium hydroxide, triethanolamine.

It is generally accepted that potassium salts are more basic than sodium salts due to the position of potassium in the periodic table of the elements relative to sodium. The enhanced alkalinity of potassium hydroxide compared to sodium hydroxide is attributed to the larger atomic radius of potassium, which leads to weaker attraction to the hydroxide counterion, enabling potassium hydroxide to ionize more readily when dissolved in aqueous solutions.

Relying on significant pH adjustment in formulations for cosmetics is undesirable. There remains a need for alkylhydroxamic acids and salts that do not require significant pH adjustment, and preferably, the alkylhydroxamic acids and salts should be considered "natural" or "sustainable" by consumers of the cosmetic formulations.

BRIEF SUMMARY OF THE INVENTION

Applicants have discovered surprisingly that potassium hydrogen salts of CHA and related $C_6$ to $C_{10}$ alkylhydroxamic acids are in fact less alkaline than their sodium counterparts. This is beneficial for the formulation of compositions where the desired pH is about 8 or less, as the formulation will require dramatically less pH adjustment for in situ generation of the alkylhydroxamic acid form.

In some embodiments, the present invention is directed to formulations comprising
a compound of Formula (I):

$$MH(AH)_2 \qquad (I),$$

wherein: M is an alkali metal cation consisting essentially of potassium,
H is hydrogen, and
AH is a $C_6$ to $C_{10}$ alkylhydroxamate anion; and
a sufficient amount of a pH adjuster to provide a pH value of the formulation of about 8 or less.

The formulation as in the preceding paragraph, wherein the pH adjuster is an organic acid.

The formulation as in any of the preceding paragraphs alone or in combination, wherein the organic acid is selected from the group consisting of: benzoic acid, sorbic acid, p-anisic acid, levulinic acid, salicylic acid, citric acid, lactic acid, malic acid, succinic acid, malonic acid, fumaric acid, anisic acid, glycolic acid, salts thereof, and combinations thereof.

The formulation as in the preceding paragraphs alone or in combination, wherein AH is caprylhydroxamate.

The formulation as in any of the preceding paragraphs alone or in combination, wherein MH(AH)2 is potassium hydrogen caprylhydroxamate.

The formulation as in any of the preceding paragraphs alone or in combination comprising from about 0.2 ppm to about 2200 ppm potassium.

The formulation as in any of the preceding paragraphs alone or in combination, wherein substantially all of the carbon present in the compound of Formula (I) is biobased.

The formulation as in any of the preceding paragraphs alone or in combination, wherein the compound of Formula (I) is present in the aqueous formulation in a solution concentration of about 0.0002% to about 2.0%, or about 0.0002% to about 1.5%, or about 0.0002% to about 1.0%, or about 0.0002% to about 0.5%.

The formulation as in any of the preceding paragraphs alone or in combination, wherein the pH value of the formulation is from about 3.5 to about 7.9, or from about 4.0 to about 7.5, or from about 4.5 to about 7.5.

The formulation as in any of the preceding paragraphs alone or in combination, wherein the formulation has a free hydroxylamine concentration of less than 1000 ppm, or less 500 ppm, or less 200 ppm, or less 100 ppm.

The formulation as in any of the preceding paragraphs alone or in combination, wherein the formulation is substantially devoid of free hydroxylamine.

The formulation as in any of the preceding paragraphs alone or in combination, wherein the formulation has a turbidity of less than about 20 NTU, or less than about 10 NTU, or less than about 5 NTU, or less than about 2.5 NTU.

The formulation as in any of the preceding paragraphs alone or in combination, wherein the formulation is or is a component of a personal care product, a home care product, a textile care product, an institutional care product, a pharmaceutical product, a veterinary product, a food product, or an industrial product.

The formulation as in any of the preceding paragraphs alone or in combination, wherein the formulation is or is a component of a personal care product selected from the group consisting of: a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer.

In other embodiments, the present invention is directed to antimicrobial compositions comprising:
a medium chain terminal diol, and
a compound of Formula (I):

$$MH(AH)_2 \quad (I),$$

wherein: M is an alkali metal cation consisting essentially of potassium,
H is hydrogen, and
AH is a $C_6$ to $C_{10}$ alkylhydroxamate anion;
a $C_6$-$C_{10}$ alkylhydroxamic acid, and
optionally an organic acid or salt thereof.

The composition as in any of the preceding paragraphs alone or in combination comprising from about 11 ppm to about 11000 ppm potassium.

The composition as in any of the preceding paragraphs alone or in combination, comprising about 0.01 wt % to about 10 wt % of the compound of Formula (I), about 10 wt % to about 80 wt % of the medium chain terminal diol, and about 1 wt % to about 20 wt % of the $C_6$-$C_{10}$alkylhydroxamic acid.

The composition as in any of the preceding paragraphs alone or in combination, wherein the medium chain terminal diol is at least one of a glyceryl monoester, a glyceryl monoether, a 1,2-alkanediol, and combinations thereof.

The composition as in any of the preceding paragraphs alone or in combination, wherein the medium chain terminal diol is a glyceryl monoester selected from the group consisting of: glyceryl monolaurate, glyceryl monocaprate, glyceryl monopelargonate, glyceryl monocaprylate, glyceryl monoheptanoate, and glyceryl monoundecylenate.

The composition as in any of the preceding paragraphs alone or in combination, wherein the medium chain terminal diol is a glyceryl monoether selected from the group consisting of: ethylhexylglycerin, methylheptylglycerin, caprylyl glyceryl ether, heptylglycerin, or cyclohexylglycerin.

The composition as in any of the preceding paragraphs alone or in combination, wherein the medium chain terminal diol is a 1,2-alkanediol selected from the group consisting of: 1,2-pentanediol, 1,2-hexanediol, 1,2-heptanediol, caprylyl glycol, and 1,2-decanediol.

The composition as in any of the preceding paragraphs alone or in combination, wherein the optional organic acid is selected from the group consisting of: benzoic acid, sorbic acid, p-anisic acid, levulinic acid, salicylic acid, citric acid, lactic acid, malic acid, malonic acid, succinic acid, fumaric acid, anisic acid, glycolic acid, salts thereof, and combinations thereof.

The composition as in any of the preceding paragraphs alone or in combination, further comprising a polyol.

The composition as in any of the preceding paragraphs alone or in combination, wherein the polyol is selected from the group consisting of: glycerin, propanediol, 1,2-propanediol (propylene glycol), 1,3-butanediol, 2,3-butanediol, 1,4-butanediol, 1,2-pentadiol, sorbitol, sorbitan, isosorbide, and combinations thereof.

The composition as in any of the preceding paragraphs alone or in combination, further comprising at least one additional ingredient selected from surfactants, emollients, humectants, conditioning agents, active agents, beaching or whitening agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin derivatives, glyceride esters, enzymes, anti-inflammatory medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof.

The composition as in any of the preceding paragraphs alone or in combination, wherein a 2% aqueous solution of the composition has a turbidity of less than about 5 NTU.

The composition as in any of the preceding paragraphs alone or in combination, wherein a 2% aqueous solution of the composition has a pH value of about 9 or less.

The composition as in any of the preceding paragraphs alone or in combination, wherein the pH value of the composition is from about 3.5 to about 7.9, or from about 4.0 to about 7.5, or from about 4.5 to about 7.5.

A formulation comprising the antimicrobial compositions as in any of the preceding paragraphs alone or in combination, wherein the antimicrobial composition is present in the formulation in a range from about 0.25 wt % to about 5.0 wt %.

The formulation as in any of the preceding paragraphs alone or in combination, wherein the antimicrobial composition is present in the formulation in a range from about 0.50 wt % to about 2.5 wt %.

The formulation as in any of the preceding paragraphs alone or in combination comprising from about 0.2 ppm to about 2200 ppm potassium.

The formulation as in any of the preceding paragraphs alone or in combination, wherein the formulation is or is a component of a personal care product, a home care product, a textile care product, an institutional care product, a pharmaceutical product, a veterinary product, a food product, or an industrial product.

The formulation as in any of the preceding paragraphs alone or in combination, wherein the formulation is or is a component of a personal care product selected from the group consisting of: a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer.

In yet other embodiments, the present invention is directed a process for preparing a formulation comprising:
preparing an aqueous solution comprising a compound of Formula (I):

MH(AH)$_2$                 (I), wherein: M is an alkali metal cation consisting essentially of potassium,
H is hydrogen, and
AH is a $C_6$ to $C_{10}$ alkylhydroxamate anion;
combining the aqueous solution with at least one other ingredient; and
adding a sufficient amount of a pH adjuster to provide a pH value of the formulation of about 8 or less, wherein the pH adjuster is added before, after, or in combination with the at least one other ingredient.

The process as in the preceding paragraph, wherein the compound of Formula (I) is present in the aqueous solution in a concentration of about 0.0002% to about 2.0%, or 0.0002% to about 1.5%, or about 0.0002% to about 1.0%, or about 0.0002% to about 0.5%.

The process as in any of the preceding paragraphs alone or in combination, wherein the adding occurs before the combining.

The process as in any of the preceding paragraphs alone or in combination, wherein the adding occurs after the combining.

The process as in any of the preceding paragraphs alone or in combination, wherein the pH adjuster is an organic acid.

The process as in any of the preceding paragraphs alone or in combination, wherein the organic acid is selected from the group consisting of: benzoic acid, sorbic acid, p-anisic acid, levulinic acid, salicylic acid, citric acid, lactic acid, malic acid, malonic acid, succinic acid, fumaric acid, anisic acid, glycolic acid, salts thereof, and combinations thereof.

The process as in any of the preceding paragraphs alone or in combination, wherein AH is caprylhydroxamate.

The process as in any of the preceding paragraphs alone or in combination, wherein MH(AH)$_2$ is potassium hydrogen caprylhydroxamate.

The process as in any of the preceding paragraphs alone or in combination, wherein substantially all of the carbon present in the compound of Formula (I) is biobased.

The process as in any of the preceding paragraphs alone or in combination, wherein the at least one other ingredient includes a medium chain terminal diol.

The process as in any of the preceding paragraphs alone or in combination, wherein the medium chain terminal diol is a glyceryl monoester, a glyceryl monoether, or a 1,2-alkanediol.

The process as in any of the preceding paragraphs alone or in combination, wherein the medium chain terminal diol is a glyceryl monoester selected from the group consisting of: glyceryl monolaurate, glyceryl monocaprate, glyceryl monocaprylate, and glyceryl undecylenate.

The process as in any of the preceding paragraphs alone or in combination, wherein the medium chain terminal diol is a glyceryl monoether selected from the group consisting of: ethylhexylglycerin, methylheptylglycerin, caprylyl glyceryl ether, heptylglycerin, or cyclohexylglycerin.

The process as in any of the preceding paragraphs alone or in combination, wherein the medium chain terminal diol is a 1,2 alkanediol selected from the group consisting of: 1,2-pentanediol, 1,2-hexanediol, caprylyl glycol, and 1,2-decanediol.

The process as in any of the preceding paragraphs alone or in combination, wherein the at least one other ingredient includes a $C_6$-$C_{10}$ alkylhydroxamic acid.

The process as in any of the preceding paragraphs alone or in combination, wherein the at least one other ingredient includes a polyol.

The process as in any of the preceding paragraphs alone or in combination, wherein the polyol is selected from the group consisting of: glycerin, propanediol, 1,2-propanediol (propylene glycol), 1,3-butanediol, 1,4-butanediol, 1,2-pentadiol, sorbitol, sorbitan, isosorbide, and combinations thereof.

The process as in any of the preceding paragraphs alone or in combination, wherein the at least one other ingredient is selected from surfactants, emollients, humectants, conditioning agents, active agents, beaching or whitening agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin derivatives, glyceride esters, enzymes, anti-inflammatory medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof.

The process as in any of the preceding paragraphs alone or in combination, wherein the pH value of the composition is from about 3.5 to about 7.9, or from about 4.0 to about 7.5, or from about 4.5 to about 7.5.

The process as in any of the preceding paragraphs alone or in combination, wherein the formulation has a turbidity of less than about 10 NTU.

The processes as in any of the preceding paragraphs alone or in combination may include preparing a formulation including the antimicrobial composition as described above.

BRIEF DESCRIPTION OF THE FIGURES AND DRAWINGS

DETAILED DESCRIPTION

Figure 1:
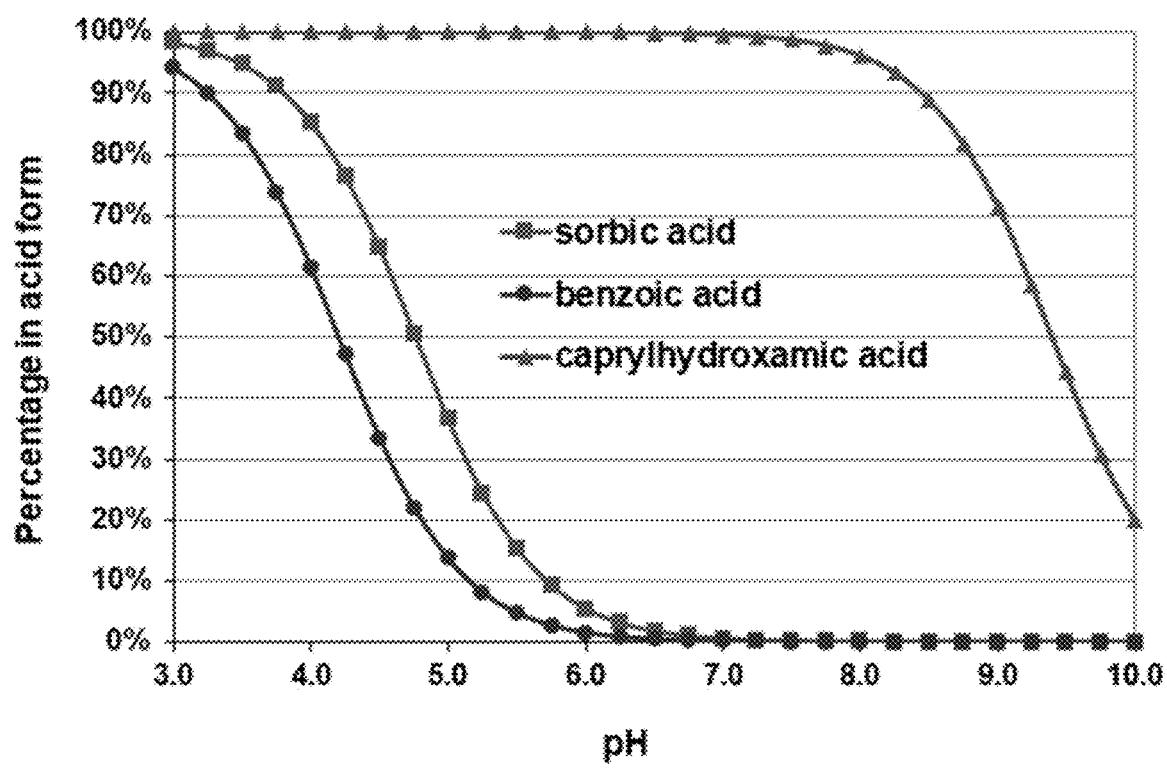
FIG. 1 illustrates the degree of ionization as a function solution pH for benzoic acid, sorbic acid, and caprylhydroxamic acid.

Before the present compounds, compositions, and methods, among others, are described, it is to be understood that this invention is not limited to the particular processes, compositions, or methodologies described, as these may vary. It is also to be understood that the terminology used in the description is for the purpose of describing the particular versions or embodiments only and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

Unless specified, "%" can refer to either a percent by weight or volume.

"Cosmetically acceptable" means suitable for use in contact with the skin without undue toxicity, incompatibility, instability, irritation, allergic response, and the like.

In some embodiments, the present invention is directed to compositions and/or formulations having antimicrobial properties. As used herein, "antimicrobial" means to inhibit the growth of unwanted microorganisms and/or to kill unwanted microorganisms to enhance product preservation.

Where applicable, chemicals are specified by their INCI Name according to the guidelines of the International Nomenclature of Cosmetic Ingredients. Additional information, including suppliers and trade names, can be found under the appropriate INCI monograph in the International Cosmetic Ingredient Dictionary and Handbook, 16th Edition published by the Personal Care Products Council, Washington, D.C., or online in the Personal Care Products Council's INCIpedia database (http://incipedia.personalcarecouncil.org).

Among the many embodiments, the present invention includes biobased compositions. Biobased or "natural" feedstocks must be used in the production of biobased compositions. An example of a biobased composition is one that is prepared from a bioderived feedstock (e.g., from current and sustainable agricultural activities, such as fermentation-, algae-, plant- or vegetable-derived; e.g., is derived from a vegetable source, preferably using a non-genetically modified organism, or biomass, and it is not petrochemically-derived (such as being derived from sustainable tree and plant farms active in the 21st century vs. fossil sources such as petroleum, natural gas, or coal). Such feedstocks are referred to herein as "natural" and "renewable" (i.e., "sustainable") and are known in the art as a non-petroleum-derived feedstock. Further, such materials are formed by "new" carbon and not from petroleum or other fossil fuel sources ("old" carbon). Such products are referred to herein as "natural" products and are known in the art as non-petrochemically-derived or "bio" products. As used herein, the term "sustainable" refers to starting materials, reaction products, compositions, and/or formulations that are derived from renewable sources. The term "sustainable" therefore is in contrast to "non-sustainable" starting materials, reaction products, compositions, and/or formulations that contain carbon from a limited natural resource, such as fossil fuel (e.g., petroleum or coal), natural gas, and the like. Thus, a natural or bio product is not petrochemically derived and/or is made from a source that is not petrochemically derived, but rather are sustainable and renewable. True natural products (bio-compounds) are formed using biomass (e.g., material stored from carbon cycle processes in living plants, roots, and the like, or released through animal respiration or refuse, or through decomposition). When carbon decomposes and is broken down over millions of years under pressure, it creates fossil fuels (the source of petrochemically-derived carbon). Bio-compounds herein are intended to include materials derived from the carbon of plant sources/biomass that exist(ed) recently and/or are sustainable, and explicitly excludes materials derived from fossil fuels.

A composition and/or formulation of the present invention can be identified and distinguished from prior art compositions and/or formulations by its biobased carbon content. In some embodiments, the biobased carbon content can be measured by radiocarbon dating to determine the relative age of materials comprised of organic (i.e., carbon-containing) matter. Radiocarbon is an unstable isotope of carbon, known as Carbon-14 (i.e., "$^{14}C$"). $^{14}C$ is an unstable isotope that emits radiation energy in the form of beta particles at a very consistent rate (i.e. a half-life for radiocarbon is 5730 years) and ultimately decays to the more stable Nitrogen-14 ($^{14}N$). Because, petroleum-based (i.e. petrochemically-derived) feedstocks are derived from plants and animals buried millions of years ago, such feedstocks' radiocarbon (i.e., $^{14}C$) has been lost to radioactive decay. The ASTM International standards provide testing standards to determine the authenticity of a "bio-based compound" using radiocarbon, which may be found in ASTM D6866-16. This standard distinguishes newer carbon from carbon derived from fossil-fuel, or petroleum- and petrochemically-derived sources, i.e., "old carbon". The amount of $^{14}C$ in recent or current biomass is known, so a percentage of carbon from a renewable source can be estimated from a total organic carbon analysis, which provides the data necessary to determine if a compound is truly derived from a "natural" and/or "sustainable" ("renewable") feedstock source or is derived conversely from a compound of "old" sequestration (i.e., a petrochemically-derived or petroleum-based source). The use of petroleum-based (also termed "fossil-based") feedstocks is generally accepted as being non-sustainable, i.e., old carbon is a non-sustainable and not a renewable feedstock and furthermore is not considered "natural" and/or "sustainable" in the art.

In some embodiments, the formulations and/or compositions of the present invention comprise biobased carbon as substantially all of the carbon present in the mixtures of compounds, which can refer to a biobased carbon content of at least 90%, at least 95%, or at least 98%.

In some embodiments, the compositions of the present invention comprise a $^{14}C$ content that is substantially equivalent to the present-day atmospheric $^{14}C$ content, as determined according to ASTM D6866. In some embodiments, the compositions of the present invention comprise a $^{14}C$ content that is at least about 90%, at least about 95%, at least about 98%, or at least about 99% of the present-day atmospheric $^{14}C$ content, as determined according to ASTM D6866. In some embodiments, the compositions of the present invention comprise at least about 0.8 $^{14}C$ atoms per $10^{12}$ carbon atoms present in the composition, at least about 1.0 $^{14}C$ atoms per $10^{12}$ carbon atoms present in the composition, or at least about 1.2 $^{14}C$ atoms per $10^{12}$ carbon atoms present in the composition, as determined according to ASTM D6866.

By "sustainable" herein, the applicants refer to materials derived from renewable sources. In contrast "non-sustainable" refers to materials from a limited natural resource, such as a fossil fuel (e.g., petroleum, natural gas, coal, and the like).

Formulations Including Potassium Hydrogen Alkylhydroxamate Salts.

In some embodiments, the present invention is directed to formulations including potassium hydrogen alkylhydroxamate salts. The formulations may be used in various applications. The formulation is, or may be a component of, a personal care product, a home care product, a textile care product, an institutional care product, a pharmaceutical product, a veterinary product, a food product, or an industrial product. In some embodiments, the formulations may be, or may be a component of, a personal care product. Personal care products include a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a foundation, lipstick, blush, eyeliner, wrinkle or anti-aging cream, mascara, a mouthwash, a toothpaste, an oral care product, a skin cleansing product, a textile cleansing product, a dish cleaning product, a hair or fur cleansing product, and a skin lotion or moisturizer.

Potassium hydrogen alkylhydroxamate salts for use with the present inventive formulations, compositions, products, and methods include, include $C_6$ to $C_{10}$ alkylhydroxamic acids, or a $C_6$ to $C_{10}$ alkylhydroxamate anion, or salts thereof. The formulations including potassium hydrogen alkylhydroxamate salts may include aqueous formulations.

The formulation including potassium hydrogen alkylhydroxamate salts can comprise a compound according to Formula (I):

$$MH(AH)_2 \quad (I)$$

wherein: M is an alkali metal cation consisting essentially of potassium,

H is hydrogen, and

AH is a $C_6$ to $C_{10}$ alkylhydroxamate anion.

The molar ratio of M to alkylhydroxamate nitrogen (N) in the potassium hydrogen alkylhydroxamate salts, $KH(AH)_2$, is preferably from about 0.3 to about 0.7, more preferably from about 0.4 to about 0.6, and even more preferably from about 0.45 to about 0.55.

M according to Formula (I) is an alkali metal cation consisting essentially of potassium. In other words, M may exclude other alkali metal cations. In some embodiments, M is devoid or substantially devoid of alkali metal cations other than potassium. Preferably, M is devoid or substantially devoid of sodium. Substantially devoid of sodium can mean that sodium is present in an amount less than 5000 ppm, preferably less than 4000 ppm, and more preferably less than 2000 ppm. In some embodiments, sodium is present in an amount less than 1000 ppm, e.g., less than 500 ppm, less than 200 ppm, or less than 100 ppm. The inventors have surprisingly found, as supported in the Examples below, that the potassium hydrogen alkylhydroxamate salts of the formulations as disclosed herein require significantly less pH adjuster. This is desirable because of ease of processing using less pH adjuster while also providing personal care products to consumers that contain minimal additives.

AH according to Formula (I) is a $C_6$ to $C_{10}$ alkylhydroxamate anion, e.g., hexanohydroxamate (caprohydroxamate), heptanohydroxamate, octanohydroxamate (caprylohydroxamate or caprylhydroxamate), nonanohydroxamate (pelargohydroxamate), decanohydroxamate (caprinohydroxamate), or combinations thereof. In some embodiments, AH according to Formula (I) is caprylhydroxamate, where the $C_6$ to $C_{10}$ alkylhydroxamate anion is a $C_8$ alkylhydroxamate. In some embodiments, where AH is caprylhydroxamate, $MH(AH)_2$ is potassium hydrogen caprylhydroxamate, $KH(C_8H_{16}O_2N)_2$.

Aqueous formulations including potassium hydrogen alkylhydroxamate salts as described above include water, e.g., deionized water. Water for an aqueous formulation according to the invention including a potassium hydrogen alkylhydroxamate salt compound and a pH adjuster can, for example, be present in an amount ranging from about 50 wt % to about 99 wt %, e.g., from 60 wt % to 99 wt %, from 70 wt % to 99 wt %, from 80 wt % to 99 wt %, from 85 wt % to 99 wt %, from 90 wt % to 99 wt %, from 95 wt % to 99 wt %, or from 98 wt % to 99 wt %. In terms of lower limits, water can be present in an amount greater than 50 wt %, e.g., greater than 60 wt %, greater than 70 wt %, greater than 80 wt %, greater than 85 wt %, greater than 90 wt %, greater than 95 wt %, or greater than 98 wt %.

The carbon present in the compound of Formula (I), as in the $C_6$ to $C_{10}$ alkylhydroxamate anion, may be biobased, as described above. In aspects, substantially all of the carbon present in the compound of Formula (I) is biobased. This is important because the compounds according to Formula (I) are useful as personal care products as described above, and non-petrochemically derived ingredients are highly regarded by consumers for their safety and efficacy.

Formulations including potassium hydrogen alkylhydroxamate salts may further include a sufficient amount of a pH adjuster to provide a pH value of the aqueous formulation of about 8 or less. In some embodiments, the pH adjuster is an organic acid.

The organic acids as described herein are of the formula R-A, where R is an organic (carbon-containing) moiety and A is an acidic group. The acid group may include a proton donor acid such as a Bronsted acid. The acid group may include a carboxylic acid (COOH), a sulfonic acid ($SO_3H$), and the like. For example, the organic acids herein may include carboxylic acids, R—COOH, where R is an organic moiety (carbon-containing). Carboxylic acids for use herein may include benzoic acid, hexanoic acid, heptanoic acid, octanoic acid, nonanoic acid, decanoic acid, dodecanoic acid, undecylinic acid, palmitic acid, isopalmitic acid, isostearic acid, stearic acid, behenic acid, and derivatives and combinations thereof.

The organic acid may be selected from the group consisting of: benzoic acid, sorbic acid, p-anisic acid, levulinic acid, salicylic acid, citric acid, lactic acid, malic acid, fumaric acid, anisic acid, glycolic acid, ethanesulfonic acid, acetic acid, salts thereof, and combinations thereof.

In some cases, the pH adjuster brings the aqueous formulation including potassium hydrogen alkylhydroxamate salts to a lower pH value than if no pH adjuster were employed in the compound. The amount of pH adjuster will depend upon the concentration of the potassium hydrogen alkylhydroxamate salts in aqueous solution. For example, the pH value of the potassium hydrogen caprylhydroxamate salts in a 1% aqueous solution is 9.0-10.0. Comparatively, the pH value of a sodium caprylhydroxamate salt in a 1% aqueous solution is 11.0-11.5. Target pH levels for the formulations as disclosed herein, e.g., for personal care products and the like, are less than pH 8. Minimal additions of the pH adjuster are required when using potassium hydrogen alkylhydroxamate salt compounds as described herein to achieve the desired pH less than 8.

By comparison, the amount of pH adjuster required when using a sodium alkylhydroxamate salt is significantly higher than with a potassium hydrogen alkylhydroxamate salt. Surprisingly, it was found that the amount of pH adjuster required when using a potassium hydrogen alkylhydroxamate salt is less than the amount of pH adjuster required when using a sodium alkylhydroxamate salt. In some embodiments, on a weight basis, formulations employing potassium hydrogen alkylhydroxamate salts require from 25 wt % to 70 wt % less pH adjuster than for formulations employing sodium alkylhydroxamate salts. The amount of pH adjuster required is formulation dependent as the requirements are also affected by other ingredients in the formula matrix. In other embodiments, on a molar basis, formulations employing potassium hydrogen alkylhydroxamate salts require from 50 mol % less pH adjuster than for formulations employing sodium alkylhydroxamate salts in order to achieve full neutralization to the acid form.

In some embodiments, pH adjuster additions alter the pH value of the aqueous formulation so that the pH value is in a range from about 3.5 to about 7.9. The pH value for an aqueous formulation according to the invention including a potassium hydrogen alkylhydroxamate salt compound and a pH adjuster can, for example, range from about 3.5 to about 7.9, e.g., from 4.0 to about 7.5, from about 4.5 to about 7.5, from about 5.0 to about 7.0, or from about 5.5 to about 6.5. In terms of upper limits, the pH adjuster additions alter the pH value of the aqueous formulation so that the pH value can be less than 8, e.g., less than 7.9, less than 7.5, less than 7.0, or less than 6.5. In terms of lower limits, the pH adjuster additions alter the pH value of the aqueous formulation so that the pH value can be greater than 3.5, e.g., greater than 4.0, greater than 4.5, greater than 5.0, or greater than 5.5.

The concentration of the compound according to Formula (I) may be variable depending upon the final formulation and/or end-use of the formulation. The compound of Formula (I) may be present in the aqueous formulation in a solution concentration of about 0.0002% to about 2.0%. The concentration of the compound of Formula (I) can, for example, be present in the aqueous formulation in a solution concentration ranging from about 0.0002% to about 2.0%, e.g., from about 0.0002% to about 1.5%, from about 0.0002% to about 1.0%, from about 0.0002% to about 0.5%, or from about 0.0002% to about 0.1%. In terms of upper limits, the solution concentration can be less than 2.0%, e.g., less than 1.5%, less than 1.0%, less than 0.5%, or less than 0.2%. In terms of lower limits, the solution concentration can be greater than 0.0002%, e.g., greater than 0.001%, greater than 0.01%, greater than 0.05%, or greater than 0.1%.

The aqueous formulations including potassium hydrogen salts of alkylhydroxamate as described herein include potassium, e.g., potassium is present in a concentration of greater than about 0.2 ppm. Potassium content may be measured by atomic absorption spectroscopy or inductively coupled plasma mass spectrometry (ICP-MS). The concentration of potassium (K) can, for example, be present in the aqueous formulations including potassium hydrogen salts of alkylhydroxamate in a concentration ranging from about 0.2 ppm K to about 2200 ppm K, e.g., from 0.2 to 2000 ppm, from 1.0 ppm to 1800 ppm, or from 10 to 1600 ppm, or from 100 to 1400 ppm. In terms of upper limits, the concentration can be less than 2200 ppm, e.g., less than 2000 ppm, less than 1800 ppm, less than 1600 ppm, less than 1400 ppm, less than 1200 ppm, or less than 1000 ppm. In terms of lower limits, the concentration can be greater than 0.2 ppm, e.g., greater than 1.0 ppm, greater than 10 ppm, greater than 100 ppm, or greater than 200 ppm.

In the formulations including potassium hydrogen alkylhydroxamate salts as described herein, it may be preferable to maintain a free hydroxylamine concentration of less than 100 ppm. Free hydroxylamine, $NH_2OH$, is an inorganic compound that is undesirable in the formulations disclosed herein due to health and safety concerns. Free hydroxylamine content may be measured by high performance liquid chromatography (HPLC) with spectroscopic detection.[5] The concentration of free hydroxylamine can, for example, be present in the formulation in a concentration ranging from about zero to about 100 ppm, e.g., from 0 to 100 ppm, from 0 ppm to 50 ppm, or from 0 to 20 ppm, or from 0 to 10 ppm. In terms of upper limits, the concentration can be less than 100 ppm, e.g., less than 80 ppm, less than 50 ppm, less than 40 ppm, less than 20 ppm, less than 10 ppm, or less than 5 ppm. In some embodiments, the formulation is devoid or substantially devoid of free hydroxylamine, e.g., less than 1 ppm. In some embodiments, the free hydroxylamine concentration can be below the limits of detection, e.g., less than 0.1 ppm.

Formulations including the compound of Formula (I) may have a turbidity of less than about 10 nephelometric turbidity units (NTU). Turbidity is important so that the formulations can readily be formulated into end-use products that are intended to be clear or transparent. Thus, the turbidity of intended clear and/or transparent formulations herein should be as low as possible for a given formulation. Turbidity is measured by nephelometric turbidimetry using an instrument such as an HF Scientific Micro 100 benchtop turbidimeter. The turbidity of the formulations including potassium hydrogen alkylhydroxamate salts can, for example, be in a range from about zero to about 20 NTU, e.g., from 0.05 NTU to 15 NTU, from 0.05 NTU to 10 NTU, or from 0.05 NTU to 5 NTU. In terms of upper limits, the turbidity can be less than 20 NTU, e.g., less than 15 NTU, less than 10 NTU, less than 5 NTU, or less than 2.5 NTU. In some embodiments, the formulation has a turbidity of less than about 1 NTU for a 2% aqueous solution in deionized water. In some embodiments, the turbidity is zero or essentially zero, e.g. below the limit of reliable detection.

Antimicrobial Compositions Comprising Potassium Hydrogen Alkylhydroxamate and Medium Chain Terminal Diols.

A multicomponent (i.e., multi-ingredient) blend is also disclosed herein and is suitable for use in formulations as an antimicrobial composition. In embodiments, the inventive antimicrobial compositions may include potassium hydrogen alkylhydroxamate salts as described above and, additionally, medium chain terminal diols (MCTD's). The potassium hydrogen alkylhydroxamate salts of these embodiments may be compounds of Formula (I) as described above. These compositions may also be used in formulations, or may be a component of, a personal care product or other uses as described above. The potassium hydrogen alkylhydroxamate salts can work synergistically with other ingredients, such as with MCTD's.

In some embodiments, the present invention is directed to antimicrobial compositions including potassium hydrogen alkylhydroxamate salts that may be used in formulations for various applications. The inventive antimicrobial composition or formulation is, or may be a component of, a personal care product, a home care product, a textile care product, an institutional care product, a pharmaceutical product, a veterinary product, a food product, or an industrial product. In some embodiments, the compositions may be used in formulations, or may be a component of, a personal care product. Personal care products include a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer.

In these embodiments, the inventive antimicrobial compositions including potassium hydrogen alkylhydroxamate salts can comprise a compound according to Formula (I), as described above, and a medium chain terminal diol, a $C_6$-$C_{10}$ alkylhydroxamic acid, and optionally an organic acid or salt thereof or other optional ingredients. The inventive antimicrobial compositions including potassium hydrogen alkylhydroxamate salts may be non-aqueous.

The most preferred diols for use in the compositions described herein when used in cosmetic, toiletry and pharmaceutical applications are medium-chain length, linear vicinal diols that demonstrate antimicrobial activity at relatively low use-levels. In some embodiments, the medium chain length is from $C_4$ to $C_{10}$ for the diols. Such diols include 1,2-pentanediol, 1,2-hexanediol, 1,2-heptanediol, caprylyl glycol, and 1,2-decanediol. Other vicinal diols useful in the compositions described herein include molecules derived from glycerin. Glycerin can be reacted with other molecules at its 1- or 3-position, leaving two vicinal hydroxyl groups. For example, glyceryl monoethers, such as ethylhexylglycerin, available commercially as Lexgard™ E from INOLEX, Inc., or methylheptylglycerin, available commercially as Lexgard™ MHG Natural MB from INOLEX Inc., are useful liquid vicinal diols having antimicrobial properties. Glyceryl monoesters such as glyceryl monolaurate, glyceryl monocaprate, glyceryl monopelargonate, glyceryl monoheptanoate, or glyceryl monocaprylate, the latter of which is commercially available as LEXGARD® GMCY from INOLEX, Inc., Philadelphia, Pa., are also useful antimicrobial vicinal diols. For the preservation of cosmetics, toiletries and pharmaceuticals, vicinal diols are known to be effective against bacteria and yeast but weak against fungi. In the book, D. Steinberg, Preservatives for Cosmetics. 2nd ed, (2006), pg. 102, the author comments regarding vicinal diols that "[t]he weakest activity on all of these is fungi." In the article, D. Smith et al., "The Self-Preserving Challenge," Cosmetic & Toiletries, No. 1, 115, No. 5 (May 2000), vicinal diols are described as having activity against bacteria, but to be "limited against *Aspergillus*." Since *Aspergillus niger*, also known as *Aspergillus brasiliensis*, is one of the microorganisms used in the CTFA challenge test, products with vicinal diols as described herein as the only preservative ingredient may not sufficiently pass the CTFA challenge test.

In some embodiments, the medium chain terminal diol is at least one of a glyceryl monoester, a glyceryl monoether, a 1,2-alkanediol, and combinations thereof. The medium chain terminal diol may be a glyceryl monoester selected from the group consisting of: glyceryl monolaurate, glyceryl monocaprate, glyceryl monopelargonate, glyceryl monocaprylate, glyceryl monoheptanoate, and glyceryl monoundecylenate. The medium chain terminal diol may be a glyceryl monoether selected from the group consisting of: ethylhexylglycerin, methylheptylglycerin, caprylyl glyceryl ether, heptylglycerin, hexylglycerin, or cyclohexylglycerin. The medium chain terminal diol may be a 1,2-alkanediol selected from the group consisting of: 1,2-pentanediol, 1,2-hexanediol, 1,2-heptanediol, caprylyl glycol, and 1,2-decanediol.

The compositions of these embodiments also include a chelating agent. Chelating agents suitable for use with the present inventive compositions, formulations, products, and methods include, but are not limited to, $C_6$ to $C_{10}$ alkylhydroxamic acids or alkylhydroxamate salts thereof, tetrasodium glutamate diacetate, phytic acid or salts thereof, gluconic acid or salts thereof, galacturonic acid or salts thereof, galactaric acid or salts thereof, and combinations thereof. In some embodiments, the chelating agent is caprylhydroxamic acid, a hydroxamate salt of caprylhydroxamic acid, or a combination thereof. In some embodiments, the chelating agent consists essentially of caprylhydroxamic acid, a hydroxamate salt of caprylhydroxamic acid, or a combination thereof.

The inventive antimicrobial compositions, and/or blends, for use in formulations include at least the following ingredients: potassium hydrogen alkylhydroxamate salts, medium chain terminal diols, and $C_6$-$C_{10}$ alkylhydroxamic acids. In some embodiments, the inventive antimicrobial compositions include from about 0.01% to about 10% of compound of Formula (I), from about 10% to about 80% of medium chain terminal diol, and from about 1% to about 20% of $C_6$-$C_{10}$ alkylhydroxamic acid, with the percent composition calculated on a weight basis. Other optional ingredients may be included in the antimicrobial compositions as described below.

The inventive antimicrobial compositions include potassium hydrogen alkylhydroxamate salts, e.g., include the compound of Formula (I), in a range from about 0.01 wt % to about 10 wt % e.g., from 0.02 wt % to 9.0 wt %, from 0.03 wt % to 8.0 wt %, from 0.04 wt % to 7.0 wt %, from 0.05 wt % to 6.0 wt %, or from 0.10 wt % to 5.0 wt %. In terms of upper limits, the amount of the compound of Formula (I) can be less than 10 wt %, e.g., less than 9.0 wt %, less than 8.0 wt %, less than 7.0 wt %, less than 6.0 wt %, or less than 5.0 wt %. In terms of lower limits, the amount of the compound of Formula (I) can be greater than 0.01 wt %, e.g., greater than 0.02 wt %, greater than 0.03 wt %, greater than 0.04 wt %, greater than 0.05 wt %, or greater than 0.10 wt %.

The inventive antimicrobial compositions include medium chain terminal diols in a range from about 10 wt % to about 80 wt %, e.g., from 15 wt % to 75 wt %, from 20 wt % to 70 wt %, from 25 wt % to 65 wt %, from 30 wt % to 60 wt %, or from 35 wt % to 55 wt %. In terms of upper limits, the amount of medium chain terminal diols can be less than 80 wt %, e.g., less than 75 wt %, less than 70 wt %, less than 65 wt %, less than 60 wt %, or less than 55 wt %. In terms of lower limits, the amount of medium chain terminal diols can be greater than 10 wt %, e.g., greater than 15 wt %, greater than 20 wt %, greater than 25 wt %, greater than 30 wt %, or greater than 35 wt %.

The inventive antimicrobial compositions include $C_6$-$C_{10}$ alkylhydroxamic acid in a range from about 1 wt % to about 20 wt %, e.g., from 1.5 wt % to 20 wt %, from 2.0 wt % to 20 wt %, from 1.0 wt % to 15 wt %, from 1.5 wt % to 15 wt %, from 2.0 wt % to 15 wt %, or from 2.5 wt % to 15 wt %. In terms of upper limits, the amount of $C_6$-$C_{10}$ alkylhydroxamic acid can be less than 20 wt %, e.g., less than 19 wt %, less than 18 wt %, less than 17 wt %, less than 16 wt %, or less than 15 wt %. In terms of lower limits, the amount of $C_6$-$C_{10}$ alkylhydroxamic acid can be greater than 1 wt %, e.g., greater than 1.0 wt %, greater than 1.5 wt %, greater than 2.0 wt %, or greater than 2.5 wt %.

Optionally, the inventive antimicrobial compositions include additional components or ingredients such as an organic acids and/or a polyol. The inventive antimicrobial compositions may include an organic acid selected from the group consisting of: benzoic acid, sorbic acid, p-anisic acid, levulinic acid, salicylic acid, citric acid, lactic acid, succinic acid, malonic acid, malic acid, fumaric acid, anisic acid, glycolic acid, salts thereof, and combinations thereof. The inventive antimicrobial compositions may include a polyol selected from the group consisting of: glycerin, propanediol, 1,2-propanediol (propylene glycol), 1,3-butanediol, 1,4-butanediol, 2,3-butanediol 1,2-pentadiol, sorbitol, sorbitan, isosorbide, and combinations thereof. The inventive antimicrobial compositions may include a medium chain ($C_6$-$C_{10}$) fatty amide of the amino acid glycine, e.g. capryloyl glycine, or a salt thereof.

Optionally, the inventive antimicrobial compositions herein can include additional components or ingredients such as include surfactants, emollients, humectants, conditioning agents, active agents, beaching or whitening agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin derivatives (e.g. glyceride esters), enzymes, anti-inflammatory and other medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof.

These components may be considered optional. In some cases, the disclosed compositions may expressly exclude one or more of the aforementioned ingredients in this section, e.g., via claim language. For example claim language may be modified to recite that the disclosed compositions, formulations, processes, etc., do not utilize or comprise one or more of the aforementioned optional ingredients.

The inventive antimicrobial composition can then be used in a subsequent formulation, such as in a formulation for a personal care product. The amount of the inventive antimicrobial compositions can, for example, be present in a formulation in a range from about 0.25 wt % to about 5.0 wt %, e.g., from 0.30 wt % to 4.5 wt %, from 0.35 wt % to 4.0 wt %, from 0.40 wt % to 3.5 wt %, from 0.45 wt % to 3.0 wt %, or from 0.50 wt % to 2.5 wt %. In terms of upper limits, the amount of the inventive antimicrobials compositions in a formulation can be less than 5.0 wt %, e.g., less than 4.5 wt %, less than 4.0 wt %, less than 3.5 wt %, less than 3.0 wt %, or less than 2.5 wt %. In terms of lower limits, the amount of the inventive antimicrobial compositions in a formulation can be greater than 0.25 wt %, e.g., greater than 0.30 wt %, greater than 0.35 wt %, greater than 0.40 wt %, greater than 0.45 wt %, or greater than 0.50 wt %.

In some embodiments, a 2% aqueous solution of the inventive antimicrobial composition has a pH value of about 9 or less. The pH value can, for example, range from about 3.5 to about 8.9, e.g., from 3.5 to about 7.9, from 4.0 to about 7.5, from about 4.5 to about 7.5, from about 5.0 to about 7.0, or from about 5.5 to about 6.5. In terms of upper limits, the pH value can be less than 9, e.g., less than 8.9, less than 8.0, less than 7.5, less than 7.0, or less than 6.5. In terms of lower limits, the pH value can be greater than 3.5, e.g., greater than 4.0, greater than 4.5, greater than 5.0, or greater than 5.5. These ranges and limits may be applicable to formulations including these compositions as well.

Compositions including potassium hydrogen alkylhydroxamate salts and medium chain terminal diols may have a lower turbidity than described above, for example, less than about 5 NTU. As with the formulations discussed above, the turbidity of the inventive antimicrobial compositions herein should be as low as possible. The turbidity of the inventive antimicrobial compositions can, for example, be in a range from about zero to about 10 NTU, e.g., from 0 NTU to 5 NTU, from 0 NTU to 2.5 NTU, from 0 NTU to 2 NTU, or from 0 NTU to 1 NTU. In terms of upper limits, the turbidity can be less than 10 NTU, e.g., less than 5 NTU, less than 2.5 NTU, less than 2 NTU, less than 1.5 NTU, less than 1 NTU, or less than 0.5 NTU. In some embodiments, the inventive antimicrobial compositions have a turbidity of less than about 1 NTU for a 2% aqueous solution in deionized water. In some embodiments, the turbidity is zero or essentially zero, e.g. below the limit of detection.

The antimicrobial compositions including potassium hydrogen salts of alkylhydroxamate as described herein include potassium (in the form of potassium ion), e.g., potassium is present in a concentration of greater than about 11 ppm. The concentration of potassium (K) can, for example, be present in the inventive antimicrobial compositions including potassium hydrogen salts of alkylhydroxamate in a concentration ranging from about 11 ppm K to about 11000 ppm K, e.g., from 11 to 10000 ppm, from 50 ppm to 9000 ppm, or from 100 to 8000 ppm, or from 200 to 7000 ppm. In terms of upper limits, the concentration can be less than 11000 ppm, e.g., less than 10000 ppm, less than 9000 ppm, less than 8000 ppm, or less than 7000 ppm. In terms of lower limits, the concentration can be greater than 11 ppm, e.g., greater than 50 ppm, greater than 100 ppm, or greater than 200 ppm.

The antimicrobial compositions as described above can be used in formulations. The formulations including antimicrobial compositions as include potassium, e.g., potassium is present in a concentration of greater than about 0.2 ppm. The concentration of potassium (K) can, for example, be present in the formulations (including antimicrobial compositions that include potassium hydrogen salts of alkylhydroxamate) in a concentration ranging from about 0.2 ppm K to about 2200 ppm K, e.g., from 0.2 to 2000 ppm, from 1.0 ppm to 1800 ppm, or from 10 to 1600 ppm, or from 100 to 1400 ppm. In terms of upper limits, the concentration can be less than 2200 ppm, e.g., less than 2000 ppm, less than 1800 ppm, less than 1600 ppm, less than 1400 ppm, less than 1200 ppm, or less than 1000 ppm. In terms of lower limits, the concentration can be greater than 0.2 ppm, e.g., greater than 1.0 ppm, greater than 10 ppm, greater than 100 ppm, or greater than 200 ppm.

Processes of Preparing Formulations Including Potassium Hydrogen Alkylhydroxamate Salts and Antimicrobial Compositions.

Formulations and antimicrobial compositions as described herein, which include potassium hydrogen alkylhydroxamate salts, are prepared by a process for preparing a formulation. In some embodiments, the process of preparing a formulation includes preparing an aqueous solution comprising a compound of Formula (I):

$$MH(AH)_2 \qquad (I),$$

wherein: M is an alkali metal cation consisting essentially of potassium,

H is hydrogen, and

AH is a $C_6$ to $C_{10}$ alkylhydroxamate anion.

The process further includes combining the aqueous solution with at least one other ingredient and adding a sufficient amount of a pH adjuster to provide a pH value of the formulation of about 8 or less. The pH adjuster can be added before, after, or in combination with the at least one other ingredient.

The process may include where the concentration of the compound according to Formula (I) may be varied depending upon the final composition and/or end-use for the formulation. The process may include that the compound of Formula (I) is present in the aqueous solution in a concentration of about 0.0002% to about 2.0%. For example, the compound of Formula (I) can be present in the aqueous solution in a concentration ranging from about 0.0002% to about 2.0%, e.g., from about 0.0002% to about 1.5%, from about 0.0002% to about 1.0%, from about 0.0002% to about 0.5%, or from about 0.0002% to about 0.1%. In terms of upper limits, the concentration can be less than 2.0%, e.g., less than 1.5%, less than 1.0%, less than 0.5%, or less than 0.2%. In terms of lower limits, the concentration can be greater than 0.0002%, e.g., greater than 0.001%, greater than 0.01%, greater than 0.05%, or greater than 0.1%. In some embodiments, substantially all of the carbon present in the compound of Formula (I) is biobased as discussed above.

The process includes combining at least one other ingredient to the compound of Formula (I) in aqueous solution. This at least one other ingredient is in addition to (i) the water of the aqueous solution and (ii) the pH adjuster to be added. The at least one other ingredient may include a medium chain terminal diol, a chelating agent, a polyol, or combinations thereof. The at least one other ingredient for combining may additionally or alternatively include additional components or ingredients as described below.

The at least one other ingredient of the process may include a medium chain terminal diol, any of which that are described above. In some embodiments, a medium chain terminal diol is combined in the process with the aqueous solution including the compound of Formula (I). In some embodiments, the medium chain terminal diol is a glyceryl monoester, a glyceryl monoether, or a 1,2-alkanediol. The medium chain terminal diol may be a glyceryl monoester selected from the group consisting of: glyceryl monolaurate, glyceryl monocaprate, glyceryl monopelargonate, glyceryl monocaprylate, glyceryl monoheptanoate, and glyceryl monoundecylenate. The medium chain terminal diol may be a glyceryl monoether selected from the group consisting of: ethylhexylglycerin, methylheptylglycerin, caprylyl glyceryl ether, heptylglycerin, or cyclohexylglycerin. The medium chain terminal diol may be a 1,2-alkanediol selected from the group consisting of: 1,2-pentanediol, 1,2-hexanediol, 1,2-heptanediol, caprylyl glycol, and 1,2-decanediol.

Chelating agents suitable for combining with the aqueous solution including the compound of Formula (I) in the present inventive process include, but are not limited to, $C_6$ to $C_{10}$ alkylhydroxamic acids or alkylhydroxamate salts thereof, tetrasodium glutamate diacetate, phytic acid or salts thereof, gluconic acid or salts thereof, galacturonic acid or salts thereof, galactaric acid or salts thereof, and combinations thereof. In some embodiments, the chelating agent is caprylhydroxamic acid, a hydroxamate salt of caprylhydroxamic acid, or a combination thereof. In some embodiments, the chelating agent consists essentially of caprylhydroxamic acid, a hydroxamate salt of caprylhydroxamic acid, or a combination thereof.

Polyols suitable for use with the present inventive process include, but are not limited to, a polyol selected from the group consisting of: glycerin, propanediol, 1,2-propanediol (propylene glycol), 1,3-butanediol, 2,3-butanediol, 1,4-butanediol, 1,2-pentanediol, sorbitol, sorbitan, isosorbide, and combinations thereof.

Optionally, the at least one other ingredient for combining in the process herein can additionally or alternatively include additional components or ingredients such as surfactants, emollients, humectants, conditioning agents, active agents, beaching or whitening agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin derivatives (e.g. glyceride esters), enzymes, anti-inflammatory and other medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof. These components may be considered optional in the process herein.

The process includes adding a sufficient amount of a pH adjuster to provide a pH value of the formulation of about 8 or less. The pH adjuster is added before, after, or in combination with the at least one other ingredient.

In some embodiments, a pH adjuster is added before the combining with the at least one other ingredient. In other embodiments, a pH adjuster is added after the combining with the at least one other ingredient. In yet other embodiments, a pH adjuster is added concurrently with the combining with the at least one other ingredient.

The pH adjuster according to the process may be an organic acid. The organic acid is selected from the group consisting of: benzoic acid, sorbic acid, p-anisic acid, levulinic acid, salicylic acid, citric acid, lactic acid, malic acid, fumaric acid, succinic acid, malonic acid, anisic acid, glycolic acid, salts thereof, and combinations thereof. Preferred organic acids include citric acid, lactic acid, and malic acid.

In some embodiments, the process includes adding a sufficient amount of a pH adjuster to affect a pH value of the formulation to be in a range from about 3.5 to about 7.9. The pH value can, for example, range from about 3.5 to about 7.9, e.g., from 4.0 to about 7.5, from about 4.5 to about 7.5, from about 5.0 to about 7.0, or from about 5.5 to about 6.5. In terms of upper limits, the pH value can be less than 8, e.g., less than 7.9, less than 7.5, less than 7.0, or less than 6.5. In terms of lower limits, the pH value can be greater than 3.5, e.g., greater than 4.0, greater than 4.5, greater than 5.0, or greater than 5.5. These ranges and limits may be applicable to formulations including the inventive antimicrobial compositions as well.

The processes may include preparing a formulation comprising the antimicrobial compositions. Yet additional ingredients as described above may be additionally combined depending upon the end-use formulation. The formulations or compositions may be a component of a personal care product, a home care product, a textile care product, an institutional care product, a pharmaceutical product, a veterinary product, a food product, or an industrial product. Personal care products producible by the process herein include a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer.

These detailed descriptions serve to exemplify the above general descriptions and embodiments which form part of the invention. These detailed descriptions are presented for illustrative purposes only and are not intended as a restriction on the scope of the invention.

EXAMPLES

Example 1

Alkali Metal Salts of Caprylhydroxamic Acid

Example 1, potassium hydrogen caprylhydroxamate, was prepared via reaction of methyl caprylate and hydroxylamine according to the procedure described by Hughes (U.S. Pat. No. 7,007,805). The resulting salt was isolated via filtration, purified by washing with methanol, and dried to a constant weight. Comparative Example 1, sodium caprylhydroxamate (sodium octanohydroxamate monohydrate, >98% as anhydrous), was purchased from TCI America and used as received.

Table 1 shows the theoretical values for the elemental compositions of Example 1 and Comparative Example 1 and the actual values as determined via elemental analysis (Galbraith Laboratories, Inc.). Elemental analysis reveals that the mole ratio of potassium to nitrogen (0.52) in Example 1 is consistent with the value expected for potassium hydrogen caprylhydroxamate (0.50), confirming that the compound of Example 1 conforms to the formula $KH(CH)_2$, where CH=caprylhydroxamate. In contrast, the mole ratio of sodium to nitrogen for Comparative Example 1 is observed to be 0.97, indicating a fully neutralized sodium salt of caprylhydroxamic acid, NaCH.

TABLE 1

Results of Elemental Analysis of Example 1 and Comparative Example 1

| Compound | Molecular Formula | wt % C | wt % H | wt % N | wt % M | wt ratio C:N | wt ratio M:N | mol ratio M:N |
|---|---|---|---|---|---|---|---|---|
| Theoretical Values ||||||||||
| Potassium Hydrogen Caprylhydroxamate | $KH(C_8H_{16}O_2N)_2$ | 53.9 | 9.3 | 7.9 | 11.0 | 6.86 | 1.40 | 0.50 |
| Potassium Caprylhydroxamate | $KC_8H_{16}O_2N$ | 48.7 | 8.2 | 7.1 | 19.8 | 6.86 | 2.79 | 1.00 |
| Sodium Caprylhydroxamate (monohydrate) | $NaC_8H_{16}O_2N \cdot H_2O$ | 48.2 | 9.1 | 7.0 | 11.5 | 6.86 | 1.64 | 1.00 |
| Actual Values ||||||||||
| E1 | $KH(C_8H_{16}O_2N)_2$ | 53.8 | 8.8 | 7.9 | 11.5 | 6.83 | 1.46 | 0.52 |
| CE1 | $NaC_8H_{16}O_2N \cdot H_2O$ | 48.3 | 8.5 | 7.0 | 11.1 | 6.91 | 1.59 | 0.97 |

Example 2

Solutions of Alkali Metal Salts of Caprylhydroxamic Acid

Figure 2:
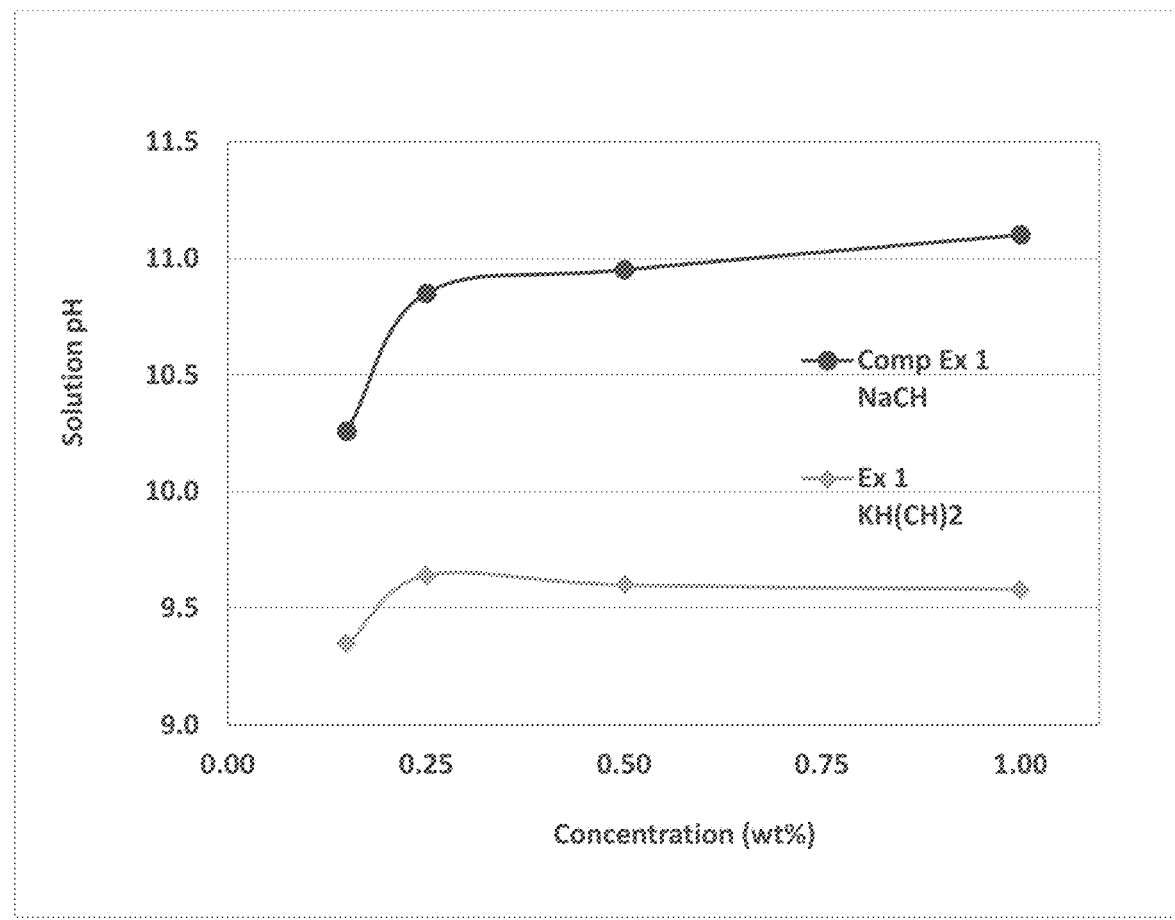
FIG. 2 illustrates solution pH as a function of concentration for NaCH and $KH(CH)_2$.

Table 2 and FIG. 2 show that aqueous solutions of potassium hydrogen caprylhydroxamate (Example 1) exhibit pH values that are ca. 0.9 to 1.5 pH units lower than those of sodium caprylhydroxamate (Comparative Example 1) at equivalent concentrations.

TABLE 2

Solution pH of alkali metal salts of caprylhydroxamic acid in deionized water.

| Concentration (%) | Solution pH | | |
|---|---|---|---|
| | Comp Ex 1 NaCH | Ex 1 KH(CH)$_2$ | Difference |
| 0.15 | 10.26 | 9.35 | 0.91 |
| 0.25 | 10.85 | 9.64 | 1.21 |
| 0.50 | 10.95 | 9.60 | 1.35 |
| 1.00 | 11.10 | 9.58 | 1.52 |

Example 3

Titration of Aqueous Solutions of Alkali Metal Salts of Caprylhydroxamic Acids

Figure 3:
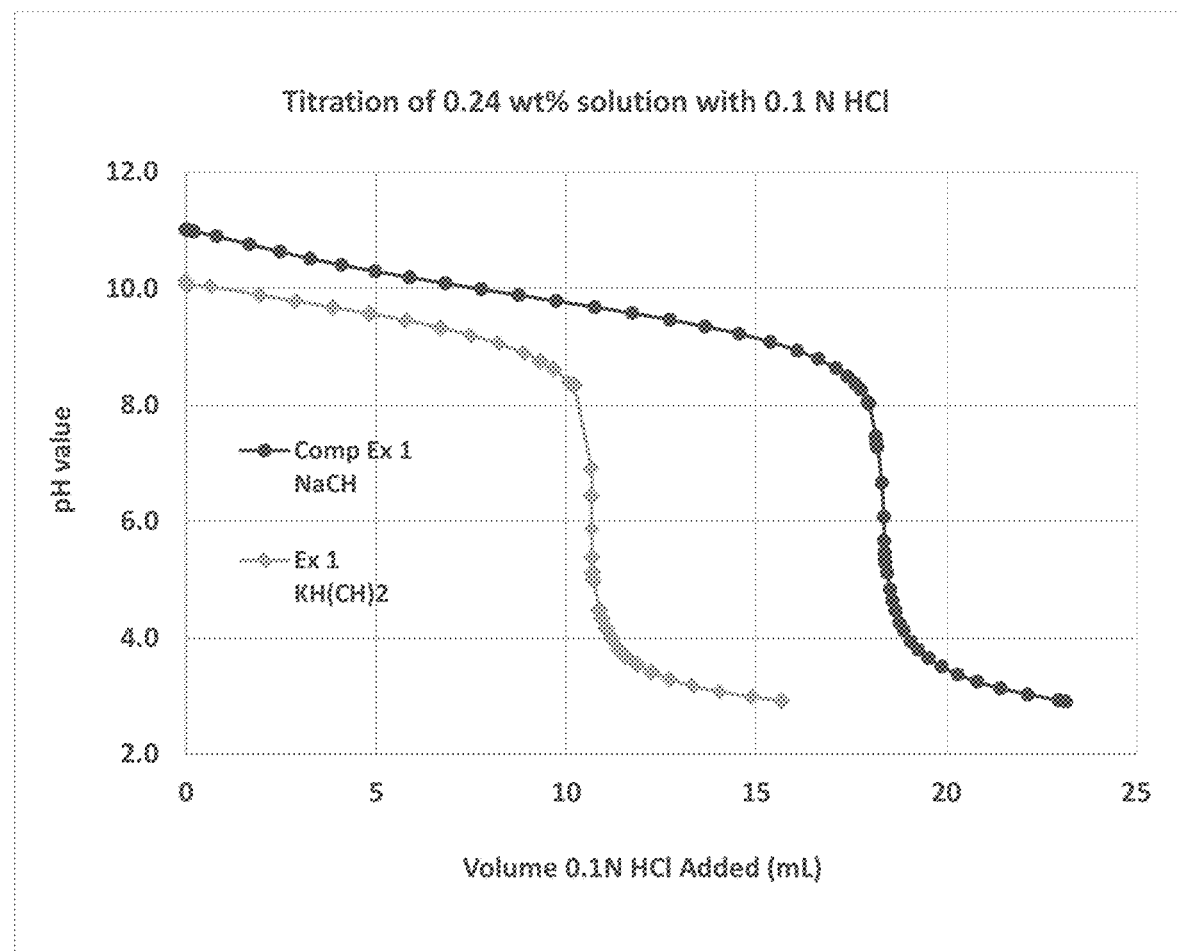
FIG. 3 illustrates titration curves for NaCH and $KH(CH)_2$.

Aqueous solutions (0.24 wt %) of KH(CH)$_2$ and NaCH were prepared by dissolving the respective compounds of Example 1 and Comparative Example 1 in deionized water. The solutions were titrated with 0.1 N HCl solution using a Metrohm autotitrator. FIG. 3 shows the titration curves for both solutions. Both the titration curves and the titration endpoints, determined to be 10.7 mL for KH(CH)$_2$ and 18.4 mL for NaCH, reveal that significantly less acid, approximately 42% less, is required to neutralize a solution of KH(CH)$_2$ when compared to a solution of NaCH at an identical concentration.

Example 4

Micellar Water Formulation Comprising Potassium Hydrogen Caprylhydroxamate

A micellar water was prepared according to the formulation in Table 3 using the following procedure: Water (95% of total water required for batch) was charged to an appropriately sized beaker of known tare weight equipped with overhead mechanical stirrer and anchor-type blade. Mixing was started at low-medium speed and potassium hydrogen caprylhydroxamate (Example 1) was added to the water and mixed until completely dissolved. Polysorbate 20, butylene glycol, and methylheptylglycerin were added to the batch and mixed until a clear, homogenous solution was formed. The formulation pH was recorded, and then citric acid (10% aqueous solution) was added to adjust the pH to 6.5±0.2, and the amount of citric acid solution required for pH adjustment was recorded. The remaining water was added in q.s. to reach 100%, and the batch was mixed until uniform and then discharged to an appropriate container for storage. Comparative Example 2 was prepared according to the same procedure, only sodium caprylhydroxamate (Comparative Example 1) was substituted for potassium hydrogen caprylhydroxamate.

Prior to pH adjustment, the micellar water formulation prepared with NaCH exhibited a significantly higher pH value compared to the formulation prepared with KH(CH)$_2$ (pH=10.34 vs. pH=9.55), and thus, the formulation prepared with KH(CH)$_2$ required 65% less citric acid for pH adjustment to the target value of pH=6.5±0.2. The turbidity values of Example 4 and Comparative Example 2 were 0.71 NTU and 0.77 NTU, respectively.

TABLE 3

Micellar water formulations of Example 4 and Comparative Example 2.

| Ingredient (INCI) | Trade Name (Supplier) | Formula Wt % (as supplied) | |
|---|---|---|---|
| | | Comp Ex 2 | Ex 4 |
| Water | Deionized Water | Q.S. to 100 wt % | Q.S. to 100 wt % |
| Polysorbate 20 | Polysorbate 20 (Making Cosmetics) | 2.00 | 2.00 |
| Butylene Glycol | Butylene Glycol (Univar Solutions) | 1.00 | 1.00 |
| Methylheptylglycerin | Lexgard Natural MHG MB (INOLEX) | 0.75 | 0.75 |
| Potassium Hydrogen Caprylhydroxamate | KH(CH)$_2$ - Example 1 | — | 0.15 |
| Sodium Caprylhydroxamate | NaCH - Comparative Example 1 | 0.15 | — |
| pH Adjuster | | | |
| Citric Acid | Citric Acid (Sigma-Aldrich), 10% aq. solution | Q.S. to pH 6.3-6.7 | Q.S. to pH 6.3-6.7 |
| Initial pH (before adjustment to specification) | | 10.34 | 9.55 |
| Amount 10% Citric Acid Solution required (wt %) | | 0.23 | 0.08 |
| Final pH (after adjustment to specification) | | 6.40 | 6.59 |

Example 5

Natural Lotion Formulation Comprising Potassium Hydrogen Caprylhydroxamate

A lotion comprising 100% biobased ingredients was prepared according to the formulation in Table 4 using the following procedure: Water (95% of total required for batch), glycerin, methylheptylglycerin, and potassium hydrogen caprylhydroxamate (Example 1) were charged to an appropriately sized beaker of known tare weight equipped with overhead mechanical stirrer and anchor-type blade and hotplate for heating. Mixing was started at low-medium speed and the xanthan gum was slowly sifted into the water phase and mixed until uniformly dispersed (no clumps remaining). The mixture was then heated to 80° C. In a separate beaker, the oil phase ingredients were combined and heated to 80° C. while mixing at low speed and mixed until uniform. The oil phase mixture was added to the water phase mixture at 80° C. while mixing at medium-high speed. Upon reaching a uniform appearance, the mixture was allowed to cool to ca. 75° C. and then homogenized at 3500 rpm for three minutes. Following homogenization, the mixture was allowed to cool to ca. 45 to 50° C. while stirring at medium speed. Upon cooling to 30° C., the formulation pH was recorded, and then citric acid (10% aqueous solution) was added to adjust the pH to 6.5±0.2, and the amount of citric acid solution required for pH adjustment was recorded. The remaining water was added in q.s. to reach 100%, and the batch was mixed until uniform and then discharged to an appropriate container for storage. Comparative Example 2 was prepared according to the same procedure, only sodium caprylhydroxamate (Comparative Example 1) was substituted for potassium hydrogen caprylhydroxamate.

Prior to pH adjustment, the lotion formulation prepared with NaCH exhibited a significantly higher pH value compared to the formulation prepared with KH(CH)$_2$ (pH=8.62 vs. pH=8.11), and thus, the formulation prepared with KH(CH)$_2$ required 36% less citric acid for pH adjustment to the target value of pH=6.5±0.2.

TABLE 4

Natural lotion formulations of Example 5 and Comparative Example 3.

| Ingredient (INCI) | Trade Name (Supplier) | Formula Wt % (as supplied) | |
|---|---|---|---|
| | | Comp Ex 3 | Ex 5 |
| Oil Phase | | | |
| Triheptanoin | SustOleo MCT (INOLEX) | 5.00 | 5.00 |
| Glyceryl Stearate SE | SustOleo GMS-SE (INOLEX) | 4.00 | 4.00 |
| Heptyl Undecylenate | LexFeel Natural (INOLEX) | 5.00 | 5.00 |
| Hydrogenated Rapeseed Oil | SustOleo TSB (INOLEX) | 3.00 | 3.00 |
| Water Phase | | | |
| Water | Deionized Water | Q.S. to 100% | Q.S. to 100% |
| Potassium Hydrogen Caprylhydroxamate | KH(CH)$_2$ - Example 1 | — | 0.15 |
| Sodium Caprylhydroxamate | NaCH - Comparative Example 1 | 0.15 | — |
| Glycerin | Glycerin, USP | 3.00 | 3.00 |
| Xanthan Gum | Keltrol CG-T (CP Kelco) | 0.30 | 0.30 |
| Methylheptylglycerin | Lexgard Natural MHG MB (INOLEX) | 1.00 | 1.00 |
| pH Adjuster | | | |
| Citric Acid | Citric acid (Sigma-Aldrich), 10% aq. solution | Q.S. to pH 6.3-6.7 | Q.S. to pH 6.3-6.7 |
| Initial pH (before adjustment to specification) | | 8.62 | 8.11 |
| Amount 10% Citric Acid Solution required (wt %) | | 0.69 | 0.44 |
| Final pH (after adjustment to specification) | | 6.68 | 6.63 |

Example 6

Natural Shampoo Formulation Comprising Potassium Hydrogen Caprylhydroxamate

Example 6 was prepared according to the formulation in Table 5. To an appropriately sized beaker of known tare weight equipped with overhead mechanical stirrer were charged water (95% of total required for batch), potassium hydrogen caprylhydroxamate (Example 1), lauryl glucoside, sodium cocoyl glutamate, cocamidopropyl betaine, and methylheptylglycerin. The batch was mixed at low to medium speed until the contents were uniform. The formulation pH was recorded, and then citric acid (10% aqueous solution) was added to adjust the pH to 6.5±0.2, and the amount of citric acid solution required for pH adjustment was recorded. The remaining water was added in q.s. to reach 100%, and the batch was mixed until uniform and then discharged to an appropriate container for storage. Comparative Example 2 was prepared according to the same procedure, only sodium caprylhydroxamate (Comparative Example 1) was substituted for potassium hydrogen caprylhydroxamate.

Prior to pH adjustment, the shampoo formulation prepared with NaCH exhibited a significantly higher pH value compared to the formulation prepared with KH(CH)$_2$ (pH=11.46 vs. pH=10.71), and thus, the formulation prepared with KH(CH)$_2$ required 29% less citric acid for pH adjustment to the target value of pH=6.5±0.2. The turbidity values of Example 6 and Comparative Example 4 were 7.30 NTU and 7.83 NTU, respectively.

TABLE 5

Natural shampoo formulations of Example 6 and Comparative Example 4.

| Ingredient - INCI Name | Trade Name (Supplier) | Formula Wt % (as supplied) | |
|---|---|---|---|
| | | Comp Ex 4 | Ex 6 |
| Water | | Q.S. to 100 wt % | Q.S. to 100 wt % |
| Potassium Hydrogen Caprylhydroxamate | KH(CH)$_2$ - Example 1 | — | 0.50 |
| Sodium Caprylhydroxamate | NaCH - Comparative Example 1 | 0.50 | — |
| Lauryl Glucoside | Plantaren 1200N UP (BASF) | 14.00 | 14.00 |
| Sodium Cocoyl Glutamate | Hostapon CGN (Clariant) | 5.00 | 5.00 |
| Cocoamidopropyl Betaine | Lexaine C (INOLEX) | 7.00 | 7.00 |
| Methylheptylglycerin | Lexgard Natural MHG MB (INOLEX) | 2.00 | 2.00 |
| pH adjuster | | | |
| Citric Acid | Citric acid (Sigma-Aldrich), 10% aq. solution | Q.S. to pH 6.4-6.8 | Q.S. to pH 6.4-6.8 |
| Initial pH (before adjustment to specification) | | 11.46 | 10.71 |
| Amount 10% Citric Acid Solution required (wt %) | | 1.68 | 1.19 |
| Final pH (after adjustment to specification) | | 6.71 | 6.70 |

Example 7

Antimicrobial Compositions with Potassium Hydrogen Caprylhydroxamate

An antimicrobial composition comprised of caprylhydroxamic acid, 1,2-hexanediol, propanediol, and potassium hydrogen caprylhydroxamate was prepared according to the formula in Table 6 according to the following procedure: To an appropriately sized beaker of known tare weight equipped with overhead mechanical stirrer were charged 1,2-hexanediol and propanediol. The mixture was heated to 40-45° C. while mixing at low speed to ensure sufficient agitation without aerating the batch. Caprylhydroxamic acid and potassium hydrogen caprylhydroxamate were slow sifted into the batch and mixed until completely dissolved. The batch was cooled and discharged to an appropriate container for storage. Comparative Example 5 was prepared in the same manner, only the potassium hydrogen caprylhydroxamate was omitted from the batch.

The antimicrobial compositions were evaluated for clarity by preparing aqueous solutions (2 wt %) in deionized water. The antimicrobial composition of Example 7 exhibited a turbidity of 0.12 NTU, whereas the antimicrobial composition of Comparative Example 5 exhibited a turbidity of 3.35 NTU. The 2% aqueous solution of Example 7 was also observed to maintain greater clarity over a 48 hour period compared to the 2% aqueous solution of Comparative Example 5.

TABLE 6

Antimicrobial Compositions of Example 7 and Comparative Example 5.

| Ingredient (INCI Name) | Trade Name (Supplier) | Formula Wt % (as supplied) | |
|---|---|---|---|
| | | Comp Ex 5 | Ex 7 |
| Potassium Hydrogen Caprylhydroxamate | $KH(CH)_2$ - Example 1 | — | 0.25 |
| Caprylhydroxamic Acid | Spectrastat CHA (INOLEX) | 5.00 | 4.75 |
| 1,2-Hexanediol | Lexgard H (INOLEX) | 30.00 | 30.00 |
| Propanediol | Zemea Propanediol (DuPont Tate & Lyle) | 65.00 | 65.00 |

Example 8

Microbiological Challenge Testing for Micellar Water Formulation Comprising $KH(CH)_2$ A micellar water formulation was prepared according to Example 8 in Table 7 using the following procedure. Deionized water was charged to an appropriately sized beaker equipped with overhead mechanical stirrer and anchor-type blade. Mixing was started at low-medium speed and polysorbate 20, butylene glycol, and $KH(CH)_2$ were added to the batch and mixed until a clear, homogenous solution was formed. Citric acid (20% aqueous solution) was added to adjust the pH to 6.5±0.1. The batch was mixed until uniform and then discharged to an appropriate container for storage.

TABLE 7

Micellar water formulations of Examples 8 and 9 and Comparative Example 6.

| Ingredient (INCI Name) | Trade Name | Ex 8 | Ex 9 | Comp Ex 6 |
|---|---|---|---|---|
| Water | Deionized Water | Q.S. to 100 wt % | Q.S. to 100 wt % | Q.S. to 100 wt % |
| Polysorbate 20 | Polysorbate 202 (Making Cosmetics) | 2.00 | 2.00 | 2.00 |
| Butylene Glycol | | 1.00 | 1.00 | 1.00 |
| Methylheptylglycerin | Lexgard Natural MHG MB (INOLEX) | — | 0.75 | — |
| Potassium Hydrogen Caprylhydroxamate | $KH(CH)_2$ - Example 1 pH Adjuster | 0.15 | 0.15 | — |
| Citric Acid | Citric Acid (Sigma-Aldrich), 20% aq. sol'n | Q.S. to pH 6.4-6.6 | Q.S. to pH 6.4-6.6 | Q.S. to pH 6.4-6.6 |

Comparative Example 6 was prepared according to the procedure used for Example 8, only $KH(CH)_2$ was omitted from the formulation.

Microbiological challenge testing ("MCT") of the micellar water formulations for Example 8 and Comparative Example 6 were performed. The challenge test complied with the USP and PCPC compendial test methodologies and was performed to determine the preservation efficacy of the potassium hydrogen caprylhydroxamate $KH(CH)_2$. The results are shown in Tables 8A-B.

TABLE 8A

MCT data for Comparative Example 6.
$Log_{10}CFU/g$

| | Staphylococcus aureus | Escherichia coli | Pseudomonas aeruginosa | Candida albicans | Aspergillus brasiliensis |
|---|---|---|---|---|---|
| Inoculum Level | 5.73 | 5.93 | 5.98 | 5.82 | 5.02 |
| Day 2 | 5.74 | 5.45 | 7.00 | 6.48 | 5.02 |
| Day 7 | <1 | 6.65 | <1 | 7.04 | 5.13 |
| Day 14 | <1 | 6.60 | 4.74 | 6.97 | 4.06 |
| Day 21 | <1 | 6.96 | 7.38 | 7.33 | 3.65 |
| Day 28 | <1 | 6.78 | 7.45 | 7.23 | 3.98 |

TABLE 8B

MCT data for Example 8.
$Log_{10}CFU/g$

| | Staphylococcus aureus | Escherichia coli | Pseudomonas aeruginosa | Candida albicans | Aspergillus brasiliensis |
|---|---|---|---|---|---|
| Inoculum Level | 5.87 | 6.94 | 5.94 | 5.76 | 5.69 |
| Day 2 | 3.30 | 1.00 | 3.60 | 3.15 | 2.94 |
| Day 7 | <1 | <1 | <1 | <1 | 1.00 |
| Day 14 | <1 | <1 | <1 | <1 | <1 |
| Day 21 | <1 | <1 | <1 | <1 | <1 |
| Day 28 | <1 | <1 | <1 | <1 | <1 |

Comparative Example 6, which contained no potassium hydrogen caprylhydroxamate, fails to meet the PCPC acceptance criteria of a 99% reduction in bacteria and 90% reduction in yeast and fungi within seven days. Example 8 containing potassium hydrogen caprylhydroxamate, $KH(CH)_2$, as an antimicrobial chelating agent to inhibit microbial growth demonstrates significant preservation efficacy. Example 8 meets and exceeds all USP, PCPC, EP-B acceptance criteria against all organisms and also meets the EP-A acceptance criteria of a 99% reduction (two-log reduction) in bacteria in two days, a 99.9% reduction (three-log reduction) of bacteria in seven days, and a 99% reduction (two-log reduction) in yeast and mold in 14 days. Example 8 and Comparative Example 6 exhibit a pH value of pH 6.5±0.1, which is considered an ideal environment for many microorganisms. Even under these conditions Example 8 demonstrates significant preservation efficacy.

Example 9

Micellar Water Formulation Comprising $KH(CH)_2$ Antimicrobial Blend

Example 9 was prepared according to the procedure used for Example 8, only that methylheptylglycerin (MHG) was added according to the formulation as in Table 7. Example 9 has the same formulation as the Example 4 formulation used above.

A challenge test complying with the USP and PCPC compendial test methodologies was performed to determine the preservation efficacy of Example 9 and the results are shown in Table 8C.

TABLE 8C

MCT data for Example 9.
$Log_{10}CFU/g$

| | Staphylococcus aureus | Escherichia coli | Pseudomonas aeruginosa | Candida albicans | Aspergillus brasiliensis |
|---|---|---|---|---|---|
| Inoculum Level | 5.87 | 5.95 | 5.93 | 5.77 | 5.70 |
| Day 2 | <1 | <1 | <1 | <1 | 3.18 |
| Day 7 | <1 | <1 | <1 | <1 | <1 |
| Day 14 | <1 | <1 | <1 | <1 | <1 |
| Day 21 | <1 | <1 | <1 | <1 | <1 |
| Day 28 | <1 | <1 | <1 | <1 | <1 |

Example 9 containing $KH(CH)_2$ and MHG demonstrated significant preservation efficacy, meeting and exceeding the USP, PCPC, EP-A, and EP-B acceptance criteria against all organisms, whereas Comparative Example 6 demonstrated very poor preservation efficacy and failed to meet acceptance criteria.

Example 10

Natural Lotion Formulation Comprising $KH(CH)_2$ Antimicrobial Blend

A lotion comprising 100% biobased ingredients was prepared according to the formulation in Table 10 using the following procedure. Water and glycerin were charged to an appropriately sized beaker equipped with overhead mechanical stirrer and anchor-type blade and hotplate for heating. Mixing was started at low-medium speed and the xanthan gum was slowly sifted into the water phase and mixed until uniformly dispersed (no clumps remaining). Methylheptylglycerin (MHG) and $KH(CH)_2$ were added. The mixture was then heated to 80° C. In a separate beaker, the oil phase ingredients were combined and heated to 80° C. while mixing at low speed and mixed until uniform. The oil phase mixture was added to the water phase mixture at 80° C. while mixing at medium-high speed. Upon reaching a uniform appearance, the mixture was allowed to cool to about 75° C. and then homogenized at 5000 rpm for three minutes. The mixture was allowed to cool to about 25° C. while stirring at medium speed. Citric acid (20% aqueous solution) was used to adjust the batch pH to 6.6±0.1. The composition was mixed until uniform and then discharged to an appropriate container for storage. The formulation of Example 10 corresponds to the formulation for Example 5 above.

TABLE 9

Natural lotion formulations of Example 10 and Comparative Example 7.

| | | Formula Wt % (as supplied) | |
|---|---|---|---|
| Ingredient (INCI) | Trade Name (Supplier) | Ex 10 | Comp Ex 7 |
| Oil Phase | | | |
| Triheptanoin | SustOleo ™ MCT (INOLEX) | 5.00 | 5.00 |
| Glyceryl Stearate SE | SustOleo ™ GMS-SE (INOLEX) | 4.00 | 4.00 |

TABLE 9-continued

Natural lotion formulations of Example 10 and Comparative Example 7.

| | | Formula Wt % (as supplied) | |
|---|---|---|---|
| Ingredient (INCI) | Trade Name (Supplier) | Ex 10 | Comp Ex 7 |
| Heptyl Undecylenate | LexFeel ™ Natural (INOLEX) | 5.00 | 5.00 |
| Hydrogenated Rapeseed Oil | SustOleo ™ TSB (INOLEX) | 3.00 | 3.00 |
| Water Phase | | | |
| Water | Deionized Water | Q.S. to 100% | Q.S. to 100% |
| Potassium Hydrogen Caprylhydroxamate | $KH(CH)_2$ - Example 1 | 0.15 | — |
| Glycerin | Glycerin, USP | 3.00 | 3.00 |
| Xanthan Gum | Keltrol ® CG-T (CP Kelco) | 0.30 | 0.30 |

TABLE 9-continued

Natural lotion formulations of Example 10 and Comparative Example 7.

| Ingredient (INCI) | Trade Name (Supplier) | Formula Wt % (as supplied) | |
|---|---|---|---|
| | | Ex 10 | Comp Ex 7 |
| Methylheptylglycerin | Lexgard Natural MHG MB (INOLEX) | 1.00 | — |
| pH Adjuster | | | |
| Citric Acid | Citric acid (Sigma-Aldrich), 20% aq. solution | Q.S. to pH 6.5-6.7 | Q.S. to pH 6.5-6.7 |

Comparative Example 7

Natural Lotion Formulation Without Methylheptylglycerin (MHG) and $KH(CH)_2$

Comparative Example 7 was prepared according to the procedure used for Example 10, except that Methylheptylglycerin (MHG) and $KH(CH)_2$ were omitted from the formula. The formulation of Comparative Example 7 corresponds to the formulation for Comparative Example 3 above.

Microbiological challenge testing (MCT) complying with the United States Pharmacopeia (USP) and PCPC compendial test methodologies was performed to determine the preservative efficacy of the $KH(CH)_2$ and MHG for Example 10 and Comparative Example 7 to determine preservative efficacy in the natural lotion formulation. [Refer to "Personal Care Products Council Technical Guidelines. Microbiology Guidelines," (2018) Personal Care Products Council, Washington, D.C.[7] and references cited therein.] The results, shown in Tables 10A-B, indicate the log value of the number of viable organisms measured after the expired time interval. The row titled "Inoculum Level" indicates the initial number of organisms present at the start of the test.

Comparative Example 7, containing no $KH(CH)_2$ and MHG, fails to meet the PCPC acceptance criteria of a 99% reduction in bacteria and 90% reduction in yeast and fungi within seven days. Example 10, containing $KH(CH)_2$ and MHG as antimicrobials to inhibit the growth of microorganisms, meet all USP 51 and PCPC acceptance criteria against all organisms and exceed the acceptance criteria for gram positive bacteria, gram negative bacteria, and yeast. Example 10 was also observed to meet the European Pharmacopeia (EP) "B" criteria (EP-B) for control of bacteria, yeast, and mold, i.e. a 99.9% reduction (three-log reduction) of bacteria in 14 days, and a 90% reduction (one-log reduction) in yeast and mold in 14 days [Refer to European Pharmacopeia (Ph. Eur.) 10.0, 2021, Section 5.1.3, Efficacy of Antimicrobial Preservation[6]].

TABLE 10A

MCT data for Comparative Example 7.
$Log_{10}CFU/g$

| | Staphylococcus aureus | Escherichia coli | Pseudomonas aeruginosa | Candida albicans | Aspergillus brasiliensis |
|---|---|---|---|---|---|
| Inoculum Level | 5.88 | 6.94 | 5.94 | 5.77 | 5.70 |
| Day 2 | 5.00 | 5.00 | 5.00 | 5.00 | 3.56 |
| Day 7 | 3.87 | 5.00 | 5.00 | 5.00 | 2.26 |
| Day 14 | 3.85 | 5.00 | 5.00 | 5.00 | 2.26 |
| Day 21 | 3.82 | 5.00 | 5.00 | 5.00 | 2.00 |
| Day 28 | 3.78 | 5.00 | 5.00 | 5.00 | 1.78 |

TABLE 10B

MCT data for Example 10.
$Log_{10}CFU/g$

| | Staphylococcus aureus | Escherichia coli | Pseudomonas aeruginosa | Candida albicans | Aspergillus brasiliensis |
|---|---|---|---|---|---|
| Inoculum Level | 5.87 | 6.94 | 5.94 | 5.76 | 5.69 |
| Day 2 | <1 | <1 | <1 | <1 | 3.15 |
| Day 7 | <1 | <1 | <1 | <1 | <1 |
| Day 14 | <1 | <1 | <1 | <1 | <1 |
| Day 21 | <1 | <1 | <1 | <1 | <1 |
| Day 28 | <1 | <1 | <1 | <1 | <1 |

The present invention is not to be limited in scope by the specific embodiments described herein. Indeed various modifications of the invention in addition to those described herein will be apparent to those skilled in the art from the foregoing description and figures. Such modifications are intended to fall within the scope of the appended claims.

It is further to be understood that all values are approximate and are provided for description. All references cited and discussed in this specification are incorporated herein by reference in their entirety and to the same extent as if each reference was individually incorporated by reference.

CITED REFERENCES

[1] M. J. Fevola, "Ingredient Profile: Benzoic Acid/Sodium Benzoate," *Cosmetics and Toiletries* 126(11):776-779 (November 2011).
[2] M. J. Fevola, "Ingredient Profile: Sorbic Acid/Potassium Sorbate," *Cosmetics and Toiletries* 127(11):756-762 (November 2012).
[3] U.S. Pat. No. 7,007,805 B2, issued Mar. 7, 2006.
[4] G. A. Hope et al., "Spectroscopic characterization of n-octanohydroxamic acid and potassium hydrogen n-octanohydroxamate," *Inorganica Chimica Acta* 363:935-943 (2010).
[5] Determination of hydroxylamine in aqueous solutions of pyridinium aldoximes by high-performance liquid chromatography with UV and fluorometric detection, W. D. Korte, *J. Chromatog. A*, 1992, 603(1-2), 145-150.
[6] "Personal Care Products Council Technical Guidelines. Microbiology Guidelines," 2018 Personal Care Products Council, Washington, D.C.

What is claimed is:

1. An aqueous formulation comprising:
   $KH(AH)_2$, wherein K is potassium, H is hydrogen, and AH is a $C_6$ to $C_{10}$ alkylhydroxamate anion; and
   an organic acid;
   wherein the formulation has a free hydroxylamine concentration of less than 200 ppm.

2. The formulation of claim 1, wherein AH is caprylhydroxamate and $KH(AH)_2$ is potassium hydrogen caprylhydroxamate.

3. The formulation of claim 1, wherein the organic acid is selected from the group consisting of: benzoic acid, sorbic acid, p-anisic acid, levulinic acid, salicylic acid, citric acid, lactic acid, malic acid, succinic acid, malonic acid, fumaric acid, anisic acid, glycolic acid, salts thereof, and combinations thereof.

4. The formulation of claim 1, wherein the $KH(AH)_2$ is present in the aqueous formulation in a solution concentration of about 0.0002% to about 2.0%.

5. The formulation of claim 1, wherein the pH value of the formulation is about 8 or less.

6. The formulation of claim 1, wherein the formulation has a free hydroxylamine concentration of less than 100 ppm.

7. The formulation of claim 1, wherein the formulation has a turbidity of less than about 20 NTU.

8. The formulation of claim 1 comprising from about 0.2 ppm to about 2200 ppm potassium.

9. The formulation of claim 1, wherein the formulation is or is a component of a personal care product, a home care product, a textile care product, an institutional care product, a pharmaceutical product, a veterinary product, a food product, or an industrial product.

10. The formulation of claim 1, wherein the formulation is or is a component of a personal care product selected from the group consisting of: a cosmetic product, a conditioner of hair, a conditioner of nails, a conditioner of skin or textiles, a shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, a lotion or cream for treating sunburn, a deodorant or an anti-perspirant, a moisturizing gel, a shaving foam, a face powder, a foundation, a lipstick, a blush, an eyeliner, a wrinkle or anti-aging cream, an eye shadow, an eyebrow pencil, a mascara, a mouthwash, a toothpaste, an oral care product, a skin cleansing product, a textile cleansing product, a dish cleaning product, a hair or fur cleansing product, and a skin lotion or moisturizer.

11. The formulation of claim 1, wherein substantially all of the carbon present in the $KH(AH)_2$ is biobased.

12. An antimicrobial composition comprising:
   a medium chain terminal diol,
   $KH(AH)_2$, wherein K is potassium, H is hydrogen, and AH is a $C_6$ to $C_{10}$ alkylhydroxamate anion; and
   a $C_6$-$C_{10}$ alkylhydroxamic acid,
   wherein the antimicrobial composition has a free hydroxylamine concentration of less than 200 ppm.

13. The composition of claim 12 comprising:
   about 0.01 wt % to about 10 wt % of the $KH(AH)_2$,
   about 10 wt % to about 80 wt % of the medium chain terminal diol, and
   about 1 wt % to about 20 wt % of the $C_6$-$C_{10}$ alkylhydroxamic acid.

14. The composition of claim 12, wherein the composition comprises from about 11 ppm to about 11000 ppm potassium.

15. The composition of claim 12, wherein the medium chain terminal diol is at least one of:
   a glyceryl monoester selected from the group consisting of: glyceryl monolaurate, glyceryl monocaprate, glyceryl monopelargonate, glyceryl monocaprylate, glyceryl monoheptanoate, and glyceryl monoundecylenate;
   a glyceryl monoether selected from the group consisting of: ethylhexylglycerin, methylheptylglycerin, caprylyl glyceryl ether, heptylglycerin, or cyclohexylglycerin;
   a 1,2-alkanediol selected from the group consisting of: 1,2-pentanediol, 1,2-hexanediol, 1,2-heptanediol, caprylyl glycol, and 1,2-decanediol;
   and combinations thereof.

16. The composition of claim 12, further comprising a polyol selected from the group consisting of: glycerin, propanediol, 1,2-propanediol (propylene glycol), 1,3-butanediol, 2,3-butanediol, 1,4-butanediol, 1,2-pentadiol, sorbitol, sorbitan, isosorbide, and combinations thereof.

17. The composition of claim 12, further comprising at least one additional ingredient selected from surfactants, emollients, humectants, conditioning agents, active agents, bleaching or whitening agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin derivatives, glyceride esters, enzymes, anti-inflammatory medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof.

18. The composition of claim 12, wherein a 2% aqueous solution of the composition has a turbidity of less than about 5 NTU and a pH value of about 8 or less.

19. A formulation comprising the composition of claim 12, wherein the composition is present in the formulation in a range from about 0.25 wt % to about 5.0 wt % and the formulation comprises from about 0.2 ppm to about 2200 ppm potassium.

20. The formulation of claim 4, wherein the formulation has a free hydroxylamine concentration from zero to 100 ppm.

21. The formulation of claim 1, wherein the formulation is devoid of free hydroxylamine.

22. An aqueous formulation comprising:
  $KH(AH)_2$, wherein K is potassium, H is hydrogen, and AH is a $C_6$ to $C_{10}$ alkylhydroxamate anion;
  wherein the formulation has a free hydroxylamine concentration of less than 200 ppm; and wherein the pH value of the formulation is about 8 or less.

* * * * *